(12) United States Patent
van Tassel et al.

(10) Patent No.: US 8,221,445 B2
(45) Date of Patent: *Jul. 17, 2012

(54) BARRIER DEVICE FOR OSTIUM OF LEFT ATRIAL APPENDAGE

(75) Inventors: Robert A van Tassel, Excelsior, MN (US); Robert G Hauser, Long Lake, MN (US)

(73) Assignee: Atritech, Inc., Plymouth, MN (US)

( * ) Notice: Subject to any disclaimer, the term of this patent is extended or adjusted under 35 U.S.C. 154(b) by 1432 days.

This patent is subject to a terminal disclaimer.

(21) Appl. No.: 10/948,217

(22) Filed: Sep. 24, 2004

(65) Prior Publication Data
US 2005/0049573 A1 Mar. 3, 2005

Related U.S. Application Data

(62) Division of application No. 10/308,032, filed on Dec. 3, 2002, now Pat. No. 6,949,113, which is a division of application No. 09/428,008, filed on Oct. 27, 1999, now Pat. No. 6,551,303.

(51) Int. Cl.
*A61M 29/00* (2006.01)

(52) U.S. Cl. ......................................... 606/200

(58) Field of Classification Search .......... 606/200, 606/108, 151, 191, 198; 623/1.11, 11.11; 604/500, 506–508, 104–106
See application file for complete search history.

(56) References Cited

U.S. PATENT DOCUMENTS 178,283 A 6/1876 French .......................... 604/109
(Continued)

FOREIGN PATENT DOCUMENTS

WO WO 93/13712 7/1993
(Continued)

OTHER PUBLICATIONS

Cragg et al., "Nonsurgical Placement of Arterial Endoprostheses: A New Technique Using Nitinol Wire," *Radiology* vol. 147, No. 1, pp. 261-263, Apr. 1983.

(Continued)

*Primary Examiner* — Gary Jackson
*Assistant Examiner* — Lindsey Bachman
(74) *Attorney, Agent, or Firm* — Seager, Tufte & Wickhem LLC

(57) ABSTRACT

A membrane applied to the ostium of an atrial appendage for blocking blood from entering the atrial appendage which can form blood clots therein is disclosed. The membrane also prevents blood clots in the atrial appendage from escaping therefrom and entering the blood stream which can result in a blocked blood vessel, leading to strokes and heart attacks. The membranes are percutaneously installed in patients experiencing atrial fibrillations and other heart conditions where thrombosis may form in the atrial appendages. A variety of means for securing the membranes in place are disclosed. The membranes may be held in place over the ostium of the atrial appendage or fill the inside of the atrial appendage. The means for holding the membranes in place over the ostium of the atrial appendages include prongs, stents, anchors with tethers or springs, disks with tethers or springs, umbrellas, spiral springs filling the atrial appendages, and adhesives. After the membrane is in place a filler substance may be added inside the atrial appendage to reduce the volume, help seal the membrane against the ostium or clot the blood in the atrial appendage. The membranes may have anticoagulants to help prevent thrombosis. The membranes be porous such that endothelial cells cover the membrane presenting a living membrane wall to prevent thrombosis. The membranes may have means to center the membranes over the ostium. Sensors may be attached to the membrane to provide information about the patient.

11 Claims, 6 Drawing Sheets

U.S. PATENT DOCUMENTS

| | | | | |
|---|---|---|---|---|
| 1,967,318 A | 7/1934 | Monahan | | 604/106 |
| 3,844,302 A | 10/1974 | Klein | | 135/26 |
| 3,874,388 A | 4/1975 | King et al. | | 606/232 |
| 4,007,743 A | 2/1977 | Blake | | 606/232 |
| 4,341,218 A | 7/1982 | Ü | | 606/195 |
| 4,585,000 A | 4/1986 | Hershenson | | 606/194 |
| 4,603,693 A | 8/1986 | Conta et al. | | 227/179.1 |
| 4,665,906 A | 5/1987 | Jervis | | 606/78 |
| 4,710,192 A | 12/1987 | Liotta et al. | | 606/108 |
| 4,917,089 A | 4/1990 | Sideris | | 606/215 |
| 4,921,484 A | 5/1990 | Hillstead | | 604/104 |
| 5,037,810 A | 8/1991 | Saliba, Jr. | | 514/56 |
| 5,041,090 A | 8/1991 | Scheglov et al. | | 604/101.02 |
| 5,041,093 A | 8/1991 | Chu | | 604/104 |
| 5,042,707 A | 8/1991 | Taheri | | 606/213 |
| 5,053,009 A | 10/1991 | Herzberg | | 604/104 |
| 5,064,435 A | 11/1991 | Porter | | 623/23.7 |
| 5,078,736 A | 1/1992 | Behl | | 623/1 |
| 5,108,420 A | 4/1992 | Marks | | 606/213 |
| 5,171,259 A | 12/1992 | Inoue | | 606/213 |
| 5,176,692 A | 1/1993 | Wilk et al. | | 606/151 |
| 5,192,301 A | 3/1993 | Kamiya et al. | | 606/213 |
| 5,256,146 A | 10/1993 | Ensminger et al. | | 604/104 |
| 5,258,042 A | 11/1993 | Mehta | | 600/36 |
| 5,284,488 A | 2/1994 | Sideris | | 606/213 |
| 5,306,234 A | 4/1994 | Johnson | | 604/49 |
| 5,334,217 A | 8/1994 | Das | | 606/213 |
| 5,350,399 A | 9/1994 | Erlebacher et al. | | 606/213 |
| 5,353,784 A | 10/1994 | Nady-Mohamed | | 600/205 |
| 5,370,657 A | 12/1994 | Irie | | 606/200 |
| 5,375,612 A | 12/1994 | Cottenceau et al. | | 128/899 |
| 5,417,699 A | 5/1995 | Klein et al. | | 606/144 |
| 5,421,832 A | 6/1995 | Lefebvre | | 264/173.11 |
| 5,425,744 A | 6/1995 | Fagan et al. | | 606/213 |
| 5,433,727 A | 7/1995 | Sideris | | 606/213 |
| 5,443,454 A | 8/1995 | Tanabe et al. | | 604/264 |
| 5,451,235 A | 9/1995 | Lock et al. | | 606/213 |
| 5,464,408 A | 11/1995 | Duc | | 606/108 |
| 5,469,867 A | 11/1995 | Schmitt | | 128/898 |
| 5,490,856 A | 2/1996 | Person et al. | | 606/151 |
| 5,522,822 A | 6/1996 | Phelps et al. | | 606/151 |
| 5,522,836 A | 6/1996 | Palermo | | 606/200 |
| 5,527,322 A | 6/1996 | Klein et al. | | 606/144 |
| 5,527,338 A | 6/1996 | Purdy | | 606/200 |
| 5,591,196 A | 1/1997 | Marin et al. | | 606/198 |
| 5,614,204 A | 3/1997 | Cochrum | | 424/423 |
| 5,634,936 A | 6/1997 | Linden et al. | | 606/213 |
| 5,634,942 A | 6/1997 | Chevillon et al. | | 623/1 |
| 5,637,097 A | 6/1997 | Yoon | | 604/174 |
| 5,643,292 A | 7/1997 | Hart | | 606/144 |
| 5,649,953 A | 7/1997 | Lefebvre | | 606/200 |
| 5,662,671 A | 9/1997 | Barbut et al. | | 606/170 |
| 5,669,933 A | 9/1997 | Simon et al. | | 600/200 |
| 5,681,347 A | 10/1997 | Cathcart et al. | | 606/200 |
| 5,690,671 A | 11/1997 | McGurk et al. | | 606/200 |
| 5,693,067 A | 12/1997 | Purdy | | 606/200 |
| 5,695,525 A | 12/1997 | Mulhauser et al. | | 623/11 |
| 5,702,421 A | 12/1997 | Schneidt | | 606/213 |
| 5,709,224 A | 1/1998 | Behl et al. | | 128/898 |
| 5,709,707 A | 1/1998 | Lock et al. | | 606/213 |
| 5,725,552 A | 3/1998 | Kotula et al. | | 606/213 |
| 5,725,568 A | 3/1998 | Hastings | | 623/11.21 |
| 5,733,294 A | 3/1998 | Forber et al. | | 606/151 |
| 5,735,290 A | 4/1998 | Sterman et al. | | 128/898 |
| 5,749,883 A | 5/1998 | Halpern | | 606/159 |
| 5,749,894 A | 5/1998 | Engelson | | 606/213 |
| 5,766,219 A | 6/1998 | Horton | | 606/191 |
| 5,769,816 A | 6/1998 | Barbut et al. | | 604/96 |
| 5,776,097 A | 7/1998 | Massoud | | 604/500 |
| 5,782,860 A | 7/1998 | Epstein et al. | | 606/213 |
| 5,800,454 A | 9/1998 | Jacobsen et al. | | 606/191 |
| 5,810,874 A | 9/1998 | Lefebvre | | 606/200 |
| 5,823,198 A | 10/1998 | Jones et al. | | 128/899 |
| 5,830,228 A | 11/1998 | Knapp et al. | | 606/195 |
| 5,836,913 A | 11/1998 | Orth et al. | | 604/107 |
| 5,836,968 A | 11/1998 | Simon et al. | | 606/200 |
| 5,846,260 A | 12/1998 | Maahs | | 606/200 |
| 5,846,261 A | 12/1998 | Kotula et al. | | 606/213 |
| 5,849,005 A | 12/1998 | Garrison et al. | | 606/1 |
| 5,851,232 A | 12/1998 | Lois | | 623/1 |
| 5,855,597 A | 1/1999 | Jayaraman | | 623/1 |
| 5,865,791 A | 2/1999 | Whayne et al. | | 604/49 |
| 5,865,802 A | 2/1999 | Yoon et al. | | 604/104 |
| 5,868,708 A | 2/1999 | Hart et al. | | 604/104 |
| 5,876,367 A | 3/1999 | Kaganov et al. | | 604/8 |
| 5,882,340 A | 3/1999 | Yoon | | 604/164.12 |
| 5,885,258 A | 3/1999 | Sachdeva et al. | | 604/530 |
| 5,895,399 A | 4/1999 | Barbut et al. | | 606/159 |
| 5,904,703 A | 5/1999 | Gilson | | 606/213 |
| 5,906,207 A | 5/1999 | Shen | | 128/898 |
| 5,910,154 A | 6/1999 | Tsugita et al. | | 606/200 |
| 5,911,734 A | 6/1999 | Tsugita et al. | | 606/200 |
| 5,916,236 A | 6/1999 | Mujis Van de Moer et al. | | 606/213 |
| 5,928,192 A | 7/1999 | Maahs | | 604/96 |
| 5,928,260 A | 7/1999 | Chin et al. | | 606/200 |
| 5,935,147 A | 8/1999 | Kensey et al. | | 606/213 |
| 5,935,148 A | 8/1999 | Villar et al. | | 606/213 |
| 5,941,249 A | 8/1999 | Maynard | | 128/898 |
| 5,947,997 A | 9/1999 | Pavcnik et al. | | 606/213 |
| 5,951,589 A | 9/1999 | Epstein et al. | | 606/213 |
| 5,954,694 A | 9/1999 | Sunseri | | 604/96 |
| 5,957,940 A | 9/1999 | Tanner et al. | | 606/155 |
| 5,976,174 A | 11/1999 | Ruiz | | 606/213 |
| 5,980,555 A | 11/1999 | Barbut et al. | | 606/200 |
| 5,989,281 A | 11/1999 | Barbut et al. | | 606/200 |
| 5,993,469 A | 11/1999 | McKenzie et al. | | 606/159 |
| 5,997,557 A | 12/1999 | Barbut et al. | | 606/159 |
| 6,007,523 A | 12/1999 | Mangosong | | 604/284 |
| 6,007,557 A | 12/1999 | Ambrisco et al. | | 606/200 |
| 6,010,517 A | 1/2000 | Baccaro | | 606/151 |
| 6,010,522 A | 1/2000 | Barbut et al. | | 606/200 |
| 6,024,754 A | 2/2000 | Engelson | | 606/213 |
| 6,024,755 A | 2/2000 | Addis | | 606/213 |
| 6,024,756 A | 2/2000 | Huebsch et al. | | 606/213 |
| 6,027,520 A | 2/2000 | Tsugita et al. | | 606/200 |
| 6,033,420 A | 3/2000 | Hahnen | | 606/185 |
| 6,036,720 A | 3/2000 | Abrams et al. | | 606/213 |
| 6,042,598 A | 3/2000 | Tsugita et al. | | 606/200 |
| 6,048,331 A | 4/2000 | Tsugita et al. | | 604/96 |
| 6,051,014 A | 4/2000 | Jang | | 606/200 |
| 6,051,015 A | 4/2000 | Maahs | | 606/200 |
| 6,056,720 A | 5/2000 | Morse | | 604/96 |
| 6,063,070 A | 5/2000 | Eder | | 606/1 |
| 6,068,621 A | 5/2000 | Balcetta et al. | | 604/500 |
| 6,074,357 A | 6/2000 | Kaganov et al. | | 604/8 |
| 6,079,414 A | 6/2000 | Roth | | 128/898 |
| 6,080,182 A | 6/2000 | Shaw et al. | | 606/213 |
| 6,080,183 A | 6/2000 | Tsugita et al. | | 606/213 |
| 6,083,239 A | 7/2000 | Addis | | 606/200 |
| 6,132,438 A | 10/2000 | Fleischman et al. | | 606/139 |
| 6,136,016 A | 10/2000 | Barbut et al. | | 606/200 |
| 6,139,527 A | 10/2000 | Laufer et al. | | 604/114 |
| 6,152,144 A * | 11/2000 | Lesh et al. | | 128/898 |
| 6,161,543 A | 12/2000 | Cox et al. | | 128/898 |
| 6,551,303 B1 * | 4/2003 | Van Tassel et al. | | 604/508 |
| 6,652,555 B1 * | 11/2003 | VanTassel et al. | | 606/200 |
| 6,652,556 B1 | 11/2003 | Van Tassel et al. | | 606/200 |
| 6,689,150 B1 * | 2/2004 | VanTassel et al. | | 606/200 |
| 6,730,108 B2 * | 5/2004 | Van Tassel et al. | | 606/200 |
| 6,949,113 B2 * | 9/2005 | Van Tassel et al. | | 606/200 |

FOREIGN PATENT DOCUMENTS

| | | |
|---|---|---|
| WO | WO 97/28749 | 8/1997 |
| WO | WO 98/02100 | 1/1998 |
| WO | WO 98/17187 | 4/1998 |
| WO | WO 99/05977 | 2/1999 |
| WO | WO 99/07289 | 2/1999 |
| WO | WO 99/08607 | 2/1999 |
| WO | WO 99/30640 | 6/1999 |
| WO | WO 00/27292 | 5/2000 |
| WO | WO 01/21247 | 3/2001 |

OTHER PUBLICATIONS

Cragg, et al., "A New Percutaneous Vena Cava Filter", *AJR*:141, 601-604, Sep. 1983.

Sugita et al., "Nonsurgical Implantation of a Vascular Ring Prosthesis Using Thermal Shape Memory Ti/Ni Alloy (Nitinol Wire)," *Trans. Am. Soc. Artif. Intern. Organs*, vol. XXXII, 30-34, 1986.

Ruttenberg, "Nonsurgical Therapy of Cardiac Disorders," *Pediatric Consult*, vol. 5, No. 2, pages not numbered, 1986.

Rashkind et al., "Nonsurgical Closure of patent ductus arteriosus: clinical application of the Rashkind PDA Occluder System," *Circulation*, vol. 75, No. 3, 583-592, Mar. 1987.

Lock et al., "Transcatheter Umbrella Closure of Congenital Heart Defects," *Circulation*, vol. 75, No. 3, 593-599, Mar. 1987.

Wessel, et al. "Outpatient Closure of the patent ductus arteriosus," *Circulation*, vol. 77, No. 5, 1068-1071, May 1988.

Lock et al., "Transcatheter Closure of Atrial Septal Defects," *Circulation*, vol. 79, No. 5, 1091-1099, May 1989.

* cited by examiner

BARRIER DEVICE FOR OSTIUM OF LEFT ATRIAL APPENDAGE

CROSS REFERENCE TO RELATED APPLICATION

This is a division of commonly-assigned application Ser. No. 10/308,032, filed Dec. 3, 2002 now U.S. Pat. No. 6,949,113, which is a division of application Ser. No. 09/428,008, filed Oct. 27, 1999, now U.S. Pat. No. 6,551,303.

BACKGROUND OF THE INVENTION

1. Field of the Invention

The invention relates to a membrane or plug structure applied to the ostium of an atrial appendage for preventing blood flow and physical connection between an atrium of the heart and the associated atrial appendage or appendages to isolate an atrial appendage and prevent thrombus leaving therefrom.

2. Description of the Related Art

There are a number of heart diseases (e.g. coronary artery disease, mitral valve disease) that have various adverse effects on the heart. An adverse effect of certain cardiac diseases, such as mitral valve disease, is atrial (or auricular) fibrillation. Atrial fibrillation way result in pooling of blood in the left atrial appendage. Blood pooling may also be spontaneous. When blood pools in the atrial appendage, blood clots can form and accumulate therein, build upon themselves, and propagate out from the atrial appendage into the atrium. These blood clots can then enter the systemic or pulmonary circulations and cause serious problems if they migrate from the atrial appendage and become free in the blood stream and embolize distally into the arterial system. Similar problems also occur when a blood clot extending from an atrial appendage into an atrium breaks off and enters the blood supply. Since blood from the left atrium and ventricle supply the heart and brain, blood clots from the atrial appendages can obstruct blood flow therein causing heart attacks, stokes or other organ ischemia. It is therefore necessary to find a means of preventing blood clots from forming in the atrial appendages and to prevent these blood clots, once formed, from leaving the atrial appendages to the heart lungs, brain or other circulations of the patient which can cause heart attacks or strokes or other organ ischemia.

U.S. Pat. No. 5,865,791 relates to the reduction of regions of blood stasis and ultimately thrombus formation in such regions, particularly in the atrial appendages of patients with atrial fibrillation. More specifically, the invention relates to procedures and devices for affixing the atrial appendages in an orientation that prevents subsequent formation of thrombus. The invention removes the appendage from the atrium by pulling on it and putting a loop around it to form a sack of the atrial appendage and then cut off from the rest of the heart.

U.S. Pat. No. 5,306,234 relates to a method for surgically closing the passage between the atrium and the atrial appendage or severing the atrial appendage.

Other methods of treatment include surgically removing the atrial appendages to prevent blood stasis in the atrial appendages.

SUMMARY OF THE INVENTION

The invention provides a membrane or plug structure for preventing blood from entering the atrial appendages to form blood clots and prevents blood clots formed in the atrial appendages from exiting therefrom which may cause heart attacks, strokes and other embolic events. The membrane covers the ostium of the atrial appendage and effectively isolates it from the atrium. It may be larger than the ostium of the appendage, and extend over an area larger than the appendage ostium. It is percutaneously delivered to the ostium of the atrial appendage by a catheter and then expanded to cover the ostium and has a means to attach the membrane over the ostium. The membrane itself may be porous or non-porous. In the case of a porous membrane, it can become infiltrated with cells so that it becomes a "living" structure, and can develop an endothelial/endocardial lining to enable it in turn to become a non-thrombogenic surface. There are many means for fixing the membrane to cover the ostium of the atrial membrane. The membrane's attachment devices have a means for self-centering the membrane over the appendage ostium. The membrane may be glued on, or have a stents or prongs which pass through the ostium and extend into or through the atrial appendage. Alternatively an anchor in the wall of the atrial appendage may be tethered to the membrane for holding the membrane in place. Springs may also extend between the anchor and the membrane to hold the membrane against the ostium. The membrane may also be connected to a tether, elastic tether or spring and placed through the atrial appendage wall for holding the membrane against the ostium and may pull on the atrial appendage such that its volume is reduced or eliminated, trapping and isolating blood clots therein. Thrombin, activated fibrinogen, or other biologic filler may be placed in the appendage after it has been sealed, with the express purpose of clotting the blood in the appendage, yet preventing clots from escaping the appendage.

Part of the device may involve a suction apparatus to remove clots that are already in place. The membrane placement may require closure of an atrial septal defect created by the placement of this appendage occluder device.

Alternatively the membrane may be held in place by a coiled spring filling the volume of the atrial appendage. The membrane may also fill the atrial appendage itself preventing blood from entering or blood clots from leaving.

The membrane itself may be porous or non-porous. In the case of a porous membrane, it can become infiltrated with cells so that it becomes a "living" structure, and can develop an endothelial/endocardial lining to enable it in turn to become a non-thrombogenic surface. It thus can develop an endothelium and with time becomes highly biocompatible. It may be heparin-coated to prevent thrombus from forming on the membrane surface, immediately after placement and until it infiltrates with cells and/or develops an endothelial covering.

The device, when implanted in the atrial appendage, may also have the ability to perform electrical monitoring of the heart. This would consist of two or more electrical contacts placed apart on the device, and connected to signal conditioning circuitry for determination of cardiac features such as rhythm of the atria or ventricles. Another sensor on the device could measure pressure of the atria, atrial appendage, or ventricular end diastolic pressures (left or right) through the open mitral or tricuspid valves. A suitable telemetry system would be used to telemeter this important electrical and hemodynamic information non-invasively outside the patient. Also, memory could be present on the device in order to record the information for later recovery via noninvasive telemetry.

This device can also be used to close fistulae or connections, elsewhere in the body, such as in the colon or bronchopulmonary systems. Another application of the device would be to seal and strengthen false aneuryms of the left ventricle by holding the membrane against the false aneurysm. The same principles apply, whereby the membrane is held against the fistulae or false aneurysm, held in place by the spring or prong mechanisms.

The device can also be used to chemically ablate the myocardial tissue of the atrial appendage in order to help limit or eliminate the electrical propagation of atrial fibrillation.

OBJECTS OF THE INVENTION

It is an object of the invention to reduce the volume of an atrial appendage to reduce the size of the region for potential blood stasis formation, and consequently the effective volume of the affected atrium.

It is an object of the invention to measure hemodynamics pressure (or flow), or electrical signals in the heart and telemeter them outside the body for diagnosis or monitoring.

It is an object of the invention to be able to close fistulae or connections elsewhere in the body, such as in the colon or bronchopulmonary systems.

It is another object of the invention for the membrane to be placed in a false aneurysm to strengthen this defect and to avoid surgery.

It is an object of the invention to reduce the region of static blood in the atrial appendages and hence the thrombogenicity of the atrium.

It is an object of the invention to prevent blood clots from forming in the atrial appendages.

It is an object of the invention to replace the ostium of the atrial appendage with a non-thrombogenic, biocompatible surface that prevents blood clots from forming.

It is an object of the invention to provide a porous membrane surface which becomes lined with endothelial or endocardial cells.

It is an object of the invention to isolate the atrial appendage from the atrium proper and prevent communication through which thrombus could migrate It is an object of the invention to minimally invasively prevent blood clots from forming in the atrial appendages and escaping therefrom.

It is an object of the invention to provide a filter between the atrium and atrial appendage to prevent blood clots from flowing therebetween.

It is an object of the invention to fill the atrial appendage with a material to prevent blood clots from leaving the atrial appendage.

It is an object of the invention to remove thrombi from the atrium via suction or other means.

It is an object of the invention to provide a means for securing a membrane over the ostium of the atrial appendage that is colonized with cells and provide a highly biocompatible surface including but not limited to endothelialization.

It is an object of the invention to prevent thrombus by use of heparin or other anti-thrombogenic substance on or eluted from the membrane.

It is an object of the invention to seal the membrane with a substance injected into the atrial appendage.

It is an object of the invention to clot the blood inside of the atrial appendage after the membrane is in place with a substance injected into the atrial appendage.

It is an object of the invention to inject a substance into the sealed appendage to ablate the myocardial cells of the appendage, in order to limit the propagation of atrial fibrillation.

It is an object of the invention to ensure the membrane is centered over the ostium of the atrial appendage.

It is an object of the invention to accurately place the membrane over the ostium of the atrial appendage.

Other objects, advantages and novel features of the present invention will become apparent from the following detailed description of the invention when considered in conjunction with the accompanying drawings.

DESCRIPTION OF THE PREFERRED EMBODIMENTS

Although atrial fibrillation results in pooling of blood in the left atrial appendage and the majority of use of the invention is anticipated to be for the left atrial appendage, the invention may also be used on the right atrial appendage and in general for any aperture in the body which needs to be blocked to prevent blood from flowing therethrough or therefrom.

Figure 4:
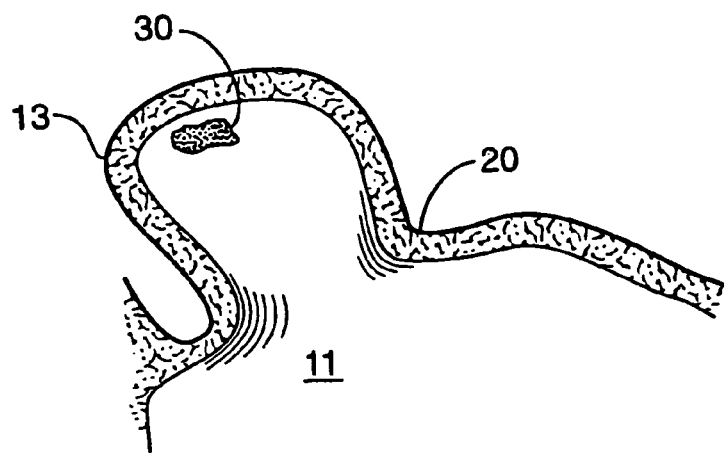
FIG. 4 is a partial cross sectional view of a portion of a heart showing an atrium and its associated atrial appendage.

As shown in FIG. 4 a thrombus 30 may occur from pooling of blood in the left atrial appendage 13 due to poor circulation of blood therein when the patient experiences atrial fibrillation. To prevent thrombus 30 from forming in the left atrial appendage 13 or to prevent thrombosis formed therein from leaving and entering the blood stream which may cause a heart attack, a stroke or ischemia, a membrane 40 is placed across the ostium 20 of the atrial appendage 13. The membrane 40 can be made of Teflon®, felt, Dacron®, silicone urethane, Gortex®, metal fibers or biocompatible polymers.

The membrane 40 may be a porous membrane. Porous membranes may consist of a biocompatible polymer which is porous, having pore sizes ranging from 20-100 microns. The pores may also be larger or smaller in rare cases. The membrane may also be a porous metal or a metal mesh of fine fibers which permit ingrowth of cells and covering with endothelial cells. The membrane may be coated with anticoagulant, or elute the anticoagulant.

The porous membrane colonizes with cells from the heart and so walls off the ostium 20 so that blood can not flow into the left atrial appendage 13 to form thrombus 30 and more importantly no thrombus 30 formed can leave the left atrial appendage 13 to cause heart attacks, strokes or ischemia.

The membrane 40 placed over the ostium 20 should be antithrombotic. In order to make the membrane antithrombotic, heparin or other anticoagulants or antiplatelet agent may be used on the membrane 40.

When porous membranes 40 are used which have an ingrowth of cells, covering the membrane with endothelial cells, the endothelial cells present a smooth cellular wall covering the membrane which prevents thrombosis from occurring at the membrane.

When blood pools in the left atrial appendage 13, thrombus 30 (blood clot) can accumulate therein, build upon themselves, and propagate out from the left atrial appendage 13 into the left atrium 11 entering the blood stream, leaving the heart and can block blood flow to the heart, brain, other organs, or peripheral vessels if it becomes lodged in the arteries thereof.

Figure 1:
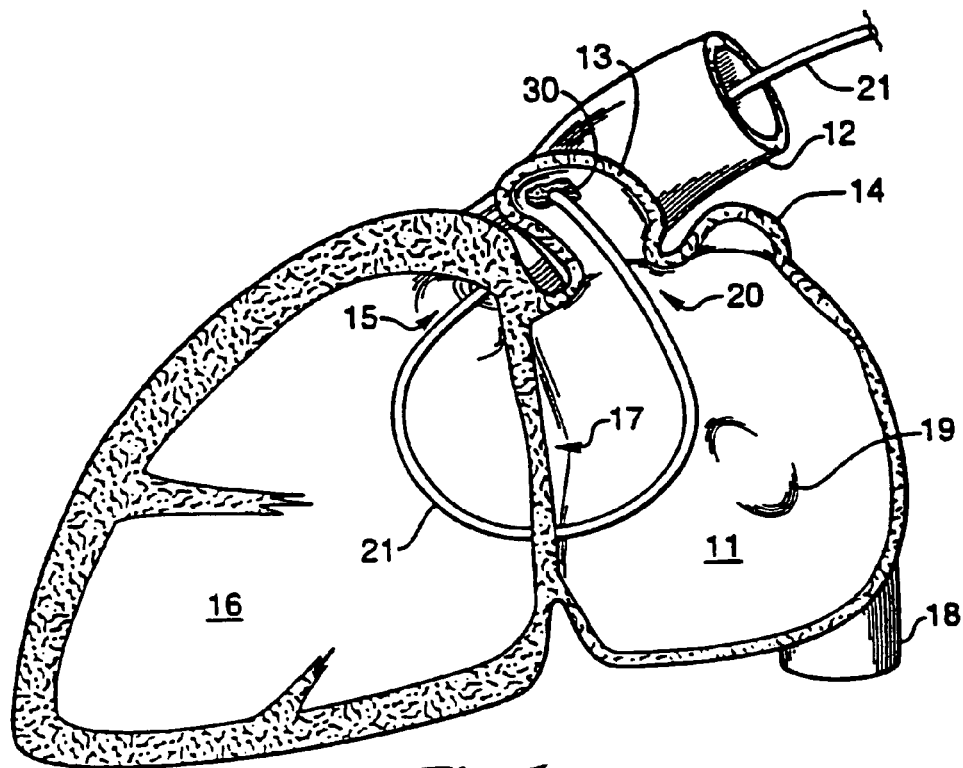
FIG. 1 is a partial cross sectional view of a heart showing a catheter entering the left atrial appendage using a retrograde procedure from the aorta.
Figure 2:
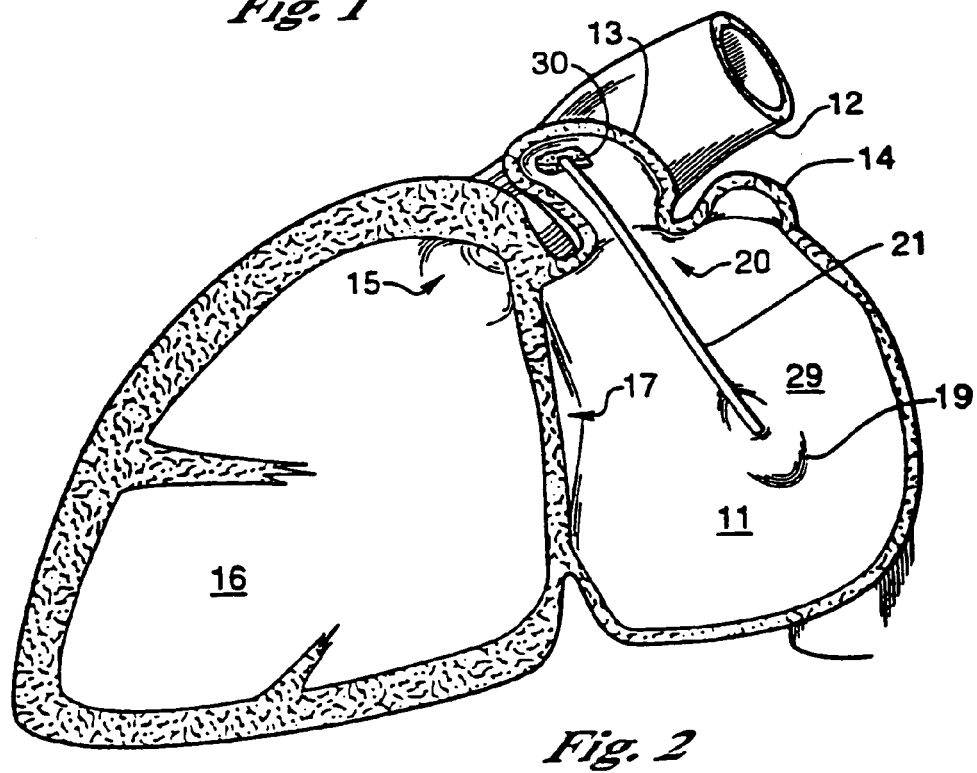
FIG. 2 is a partial cross sectional view of a heart showing a catheter entering the left atrial appendage using a transeptal procedure from the femoral vein or superior vena cava.

FIGS. 1 and 2 show a cross section of a human heart showing a thrombus 30 in the left atrial appendage 13. The figures also show the atrial appendage ostium 20 which is to have a membrane 40 placed over it to prevent the thrombus 30 from escaping out of the atrial appendage 13 into the left atrium 11 and thus into the blood stream, which could cause a stroke, a heart attack or ischemia. The membrane 40 also prevents blood from entering the left atrial appendage 13 where it could pool due to poor circulation and become a thrombus.

Figure 3:
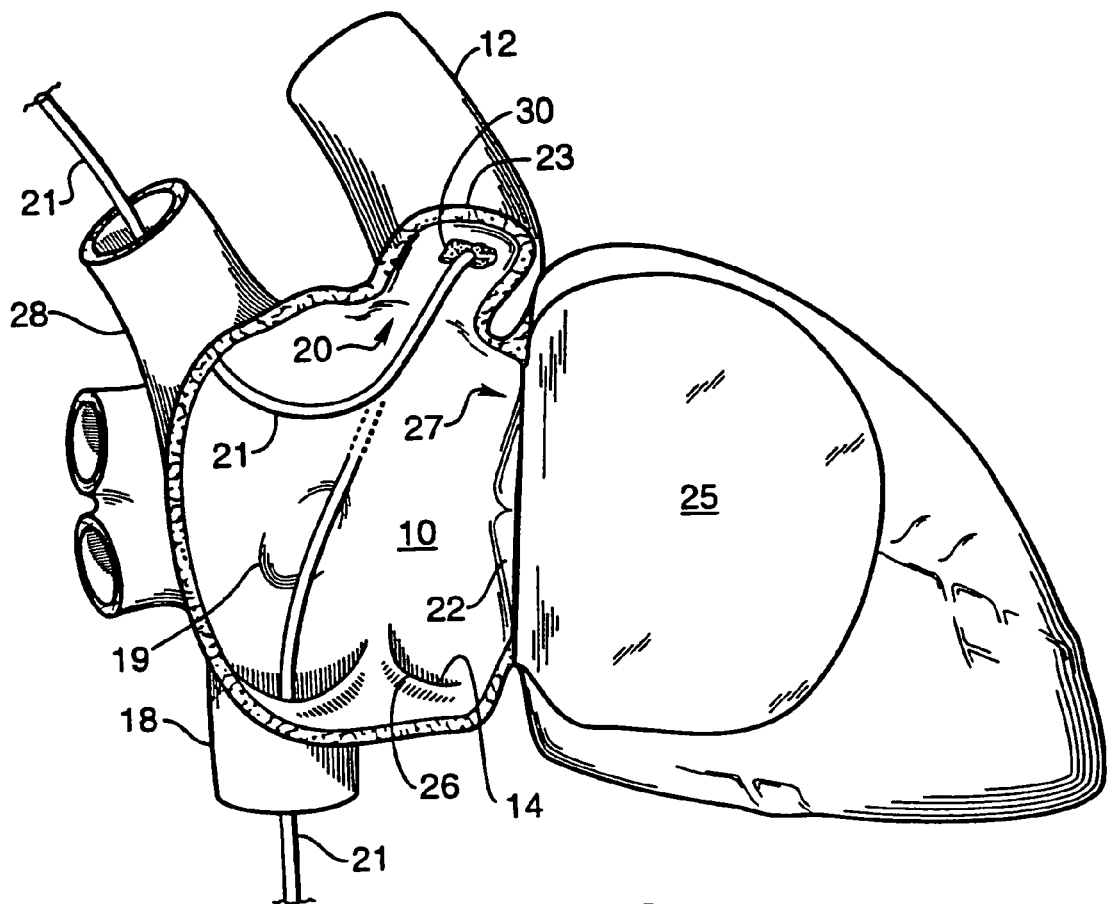
FIG. 3 is a partial cross sectional view of a heart showing a catheter entering the right atrial appendage from the jugular vein or optionally from the femoral vein.

FIG. 3 shows a cross section of a human heart showing a thrombus 30 in the right atrial appendage 23. The right atrial appendage 23 can be treated in the same manner as the left atrial appendage 13.

FIG. 4 shows a cross section of the left atrium 11, the ostium 20 and the left atrial appendage 13 having a thrombus 30 therein.

Figure 5:
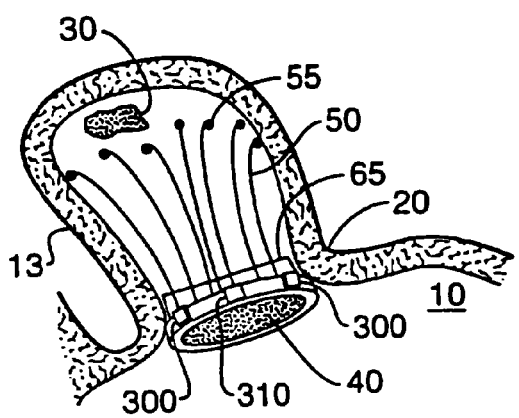
FIG. 5 is a partial cross sectional view of a portion of a heart showing an atrium and its associated atrial appendage with a porous membrane having flexible wire prongs with atraumatic bulbs to hold the membrane in place and electronics built into the membrane.

FIG. 5 shows a first embodiment of the invention wherein the porous membrane 40 has a plurality of flexible prongs 50 which may be made from a shape memory alloy, such as Nitinol®, for retaining a predisposed shape. The prongs 50 may be atraumatic so that they do not perforate the left atrial appendage 13. The prongs 50 may have atraumatic bulbs 55 on their tips so that the tips of the prongs 50 will not perforate the left atrial appendage 13. Nitinol® has the property of being able to be placed in a catheter in a compact configuration and then expanded when released from the catheter to a predetermined memory shape. The shape selected may be for the prongs 50 to curve around the lip of the ostium 20 and then hug the sides of the left atrial appendage 13. In this manner the membrane 40 will securely block the ostium 20 preventing blood from entering and particularly for preventing thrombosis 30 from leaving the left atrial appendage 13.

The membrane 40 is self centering over the ostium 20 of the left atrial appendage 13, by placing the prongs 50 in a circle around the membrane 40 such that the prongs 50 fit against the wall of the left atrial appendage 13 of or within the lumen of the ostium 20 to center the membrane 40 over the ostium 20. The membrane 40 may also be centered by a centering rim 65 (see FIG. 6) attached to the back (appendage) side of the membrane 40 that protrudes into the ostium 20 for centering. The centering rim 65 has a diameter of less than the diameter of the membrane 40. The centering means may also consist of a series of centering cables 66 (see FIG. 11) which attach to a spring 90 or tether 85 from the centering rim 65 or the membrane 40, to assure that centering occurs with placement.

Optionally electronics, such as sensors 300 and chips 310, built into the membrane may be used to provide data about hemodynamics pressure, flow rates, temperature, heart rates, and electrical signals in the heart. When the membrane is placed in the left atrial appendage 13 the sensors 300 may measure pressures in the atria or atrial appendage. The sensors may also measure ventricular end diastolic pressures through the open mitral or cuspid valves. Other information about the heart may be gathered such as noise from accelerometers to detect leakage, valve efficiency, activity levels of the patient and other noise related date. The sensors 300 may also be blood oxygen sensors. The chip 310 may use telemetry to transmit the information gathered by the sensors 300 and processed or stored by the chip 310 to receiving devices to aid in the treatment of the patient.

Figure 6:
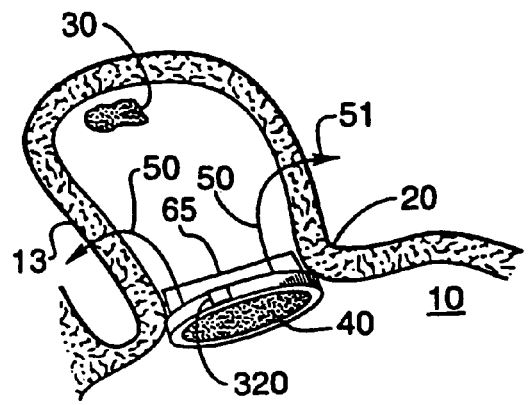
FIG. 6 is similar to FIG. 5 with the atraumatic bulbs removed so that the flexible wire prongs may puncture the atrium wall and secure the membrane to the atrial appendage and a centering rim added to the membrane.

In FIG. 6 the protective bulbs 55 are removed from the flexible prongs 50 of FIG. 5 such that flexible prongs 50 puncture the walls of the left atrial appendage 13 and secure the membrane 40 in place. The flexible prongs 50 may penetrate into the atrial appendage wall or extend through the atrial appendage wall. The prongs may have based ends 51 to prevent the prongs from withdrawing from the atrial appendage wall.

The membrane 40 has centering rim 65 attached for centering the membrane in the ostium 20 and marker 320 in the membrane 40 for observing the position of the membrane while it is being inserted. The marker may be used for x-ray or ultrasound observation.

Although Nitinol® was cited above as a type of shape memory alloy prong material which can be used, any type of memory alloy may be used. Such alloys tend to have a temperature-induced phase change which will cause the material to have a preferred configuration when heated above a certain transition temperature. Other metals which may be used as prongs include corrosion resistant spring metals such as Elgiloy® or spring tempered steel.

Figure 7:
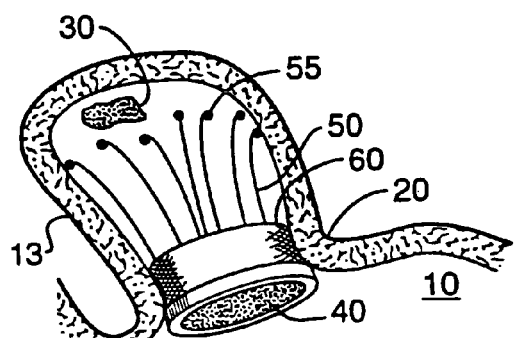
FIG. 7 is a partial cross sectional view of a portion of a heart as in FIG. 5 with a stent portion between the membrane and the prongs.

Another embodiment of the invention is shown in FIG. 7. It is similar to the embodiment shown in FIG. 5. The embodiment in FIG. 7 has a stent 60 attached to the membrane 40 for expanding in the ostium 20 helping to secure the membrane 40 thereto. The prongs 50 operate in the same manner as in FIG. 5 hugging the inner walls of the left atrial membrane 13 to secure the membrane 40 to cover the ostium 20. The stent 60 may also be made from Nitinol®, Elgiloy® or another expandable spring loaded or balloon expandable material.

The membrane 40 may be self centering over the ostium 20 of the left 13 atrial appendage, by placing the stent 60 into the ostium wherein the stent plugs the ostium with the membrane 40 centered in the stent. Further the prongs 50 fit against the wall of the left atrial appendage 13 of or within the lumen of the ostium 20 to center the membrane 40 over the ostium 20.

Figure 8:
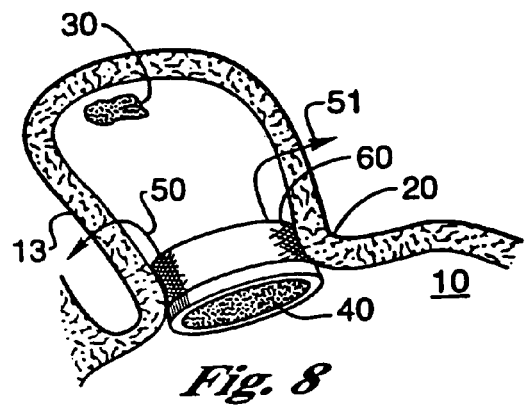
FIG. 8 is the same as FIG. 7 with the atraumatic bulbs removed so that the flexible wire prongs may puncture the atrium wall and secure the membrane to the atrial appendage.

In FIG. 8 the protective bulbs 55 are removed from the flexible prongs 50 of FIG. 7 such that flexible prongs 50 puncture the walls of the left atrial appendage 13 and secure the membrane 40 in place. The flexible prongs 50 may penetrate into the atrial appendage wall or extend through the atrial appendage wall. The prongs may have barbed ends 51 to prevent the prongs from withdrawing from the atrial appendage wall.

Figure 9:
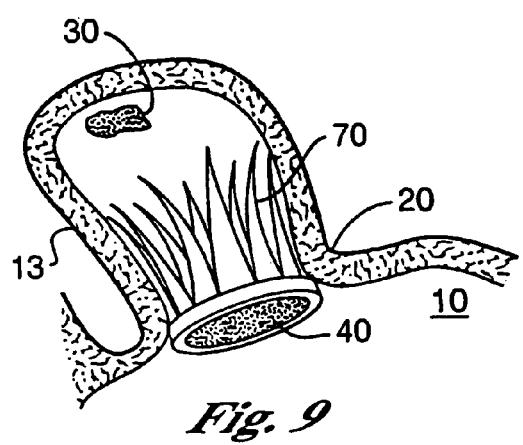
FIG. 9 is a partial cross sectional view of a portion of a heart showing an atrium and its associated atrial appendage with a porous membrane having a large expandable stent to hold the membrane in place.

In the embodiment shown in FIG. 9 a larger expandable stent 70 is used to both engage the sides of the ostium 20 and hug the inside walls of the left atrial membrane 13. Again the stent may be made of Nitinol®, Elgiloy® or other material which may be delivered in a catheter and expanded to the proper size and shape to securely hold the membrane 40 over the ostium 20 to prevent blood from entering the left atrial appendage 13 and for preventing thrombosis 30 from exiting.

Figure 10:
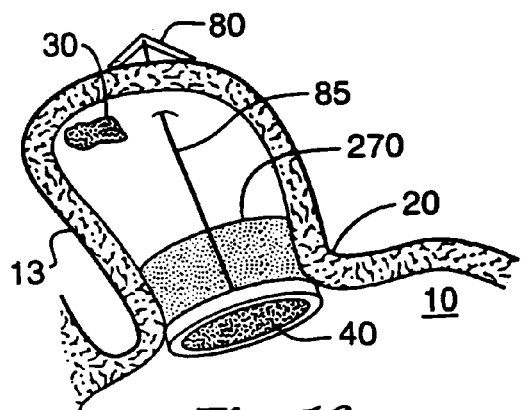
FIG. 10 is a partial cross sectional view of a portion of a heart showing an atrium and its associated atrial appendage having an anchor and a tether to hold the membrane in place.

FIG. 10 shows another embodiment of the invention wherein the membrane 40 is secured over the ostium 20 by means of an anchor 80 which is driven into or through the wall of the left atrial appendage 13 and secured therein by the surface area of the anchor so that it will not pull out of or through the wall of the left atrial appendage 13 or cause embolism from the left atrial appendage 13. A tether 85 is attached to the anchor 80 and to the membrane 40 to secure the membrane 40 snuggly against the ostium 20. A substance 270 such as thrombin, activated fibrinogen, or other biologic filler may be placed in the left atrial appendage 13 by injection through a catheter after the membrane 40 is in place such that blood is clotted in the atrial appendage so that it can not escape. The device delivery catheter itself may have a port for this injection. The port may also be used to inject contrast such as echocardiographic contrast that can be immediately visualized, and examined to determine whether there is a good seal between the ostium of the appendage and the device. The substance 270 injected into the atrial appendage may also be a sealant or filler to seal the membrane against leakage from the atrial appendage. The sealant material, filler material or blood clotting material may be used with any of the embodiments of the invention.

In another embodiment the catheter may inject a chemical ablation agent such as ethanol to ablate the myocardial cells in the sealed off atrial appendage 13 and thus limit atrial fibrillation by limiting or eliminating electrical propagation in the atrial appendage.

Figure 11:
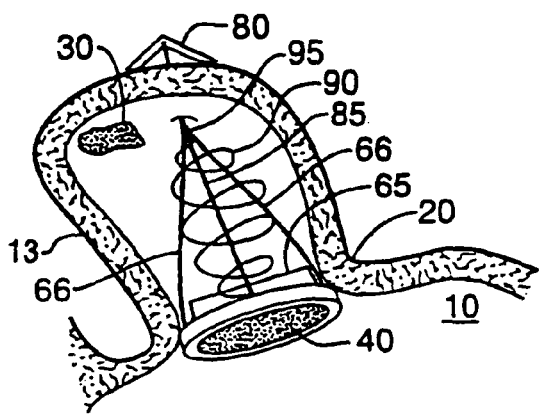
FIG. 11 is a partial cross sectional view of a portion of a heart showing an atrium and its associated atrial appendage having an anchor and a spring to hold the membrane in place, a centering rim on the membrane and a centering cable.
Figure 12:
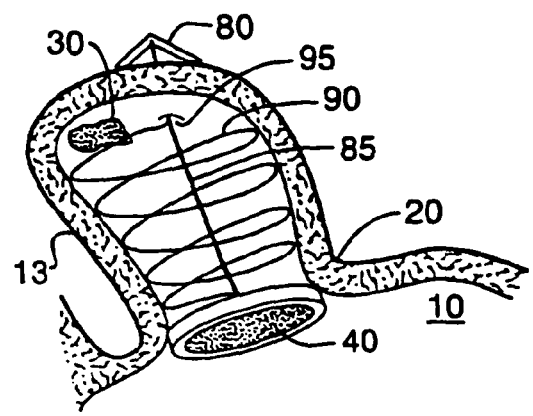
FIG. 12 is the same as FIG. 11 with the spring filling the atrium to help hold the membrane in pace.

FIG. 11 shows another embodiment of the invention wherein membrane 40 has a spiral spring 90 in addition to the anchor 80. The spiral spring 90 can be used in conjunction with or separately from the tether 85 to pull the membrane 40 against the ostium 20. Although a spiral spring 90 has been shown in FIG. 11, the shape used may be oval, cylindrical, oblong, or other shape to connect the anchor 80 to the membrane 40. In another embodiment shown in FIG. 12 the spiral spring 90 may fill the volume of the left atrial appendage 13 securing the membrane 40 to the ostium 20. The spiral spring 90 filling the left atrial appendage 13 may also have an anchor 80 and tether 85 to help secure the membrane 40 to the ostium 20. Alternatively centering rim 65 may be used as shown in FIG. 11 to center the membrane 40 over ostium 20 of left atrial appendage 13. Centering cables 66 connected to spring 90 and either membrane 40 or centering rim 65 may also be used to center the membrane 40 over the ostium 20.

Figure 13:
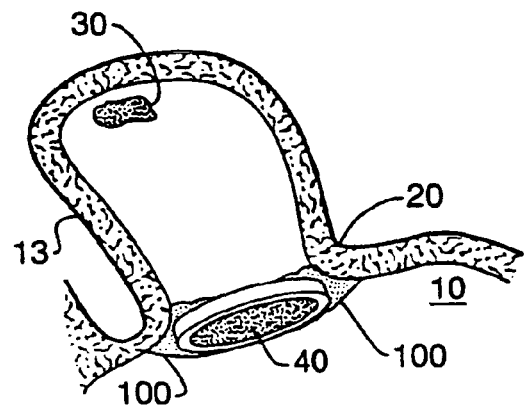
FIG. 13 is a partial cross sectional view of a portion of a heart showing an atrium and its associated atrial appendage with the membrane adhesively being held in place.

FIG. 13 shows yet another means of securing the membrane 40 over the ostium 20. In this embodiment membrane 40 is directly attached to the ostium 20 by an adhesive 100.

Figure 14:
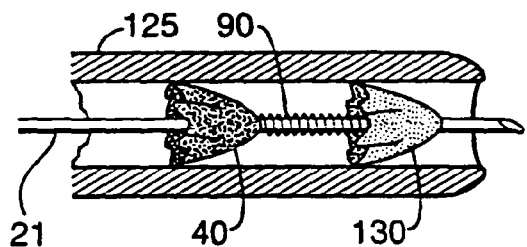
FIG. 14 is a partial cross sectional view of a delivery catheter having a disk, a spring and membrane therein.
Figure 15:
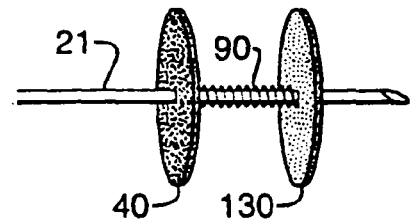
FIG. 15 is a schematic view of a disk, spring and membrane after being expanded out of the delivery catheter of FIG. 11.

FIG. 14 shows a delivery catheter 125 containing a collapsed porous membrane 40 and a collapsed disk 130 connected to the porous membrane 40 by a spring 90 on catheter 21. The disk 130 may be made of a flexible woven metal or a flexible woven metal with a thin porous polymer sandwiched inside. Disk 130 may also be a polymer weave. The disk 130 is flexible and compresses or folds so it fits into the delivery catheter 125 and expands to its desired shape after release from the delivery catheter 125. Similarly membrane 40 compresses or folds to fit into the delivery catheter 125 and expands to its desired shape after release. FIG. 15 shows the porous membrane 40, disk 130 and spring 90 from FIG. 14 in an expanded configuration outside of the delivery catheter 125.

FIG. 15 shows the spring 90 connecting the porous membrane 40 and the disk 130 for urging them together. In other embodiments an elastic tether or a tether with teeth and a pawl on the porous membrane 40 to form a ratchet can also be used to pull the porous membrane 40 and the disk 130 together.

Figure 16:
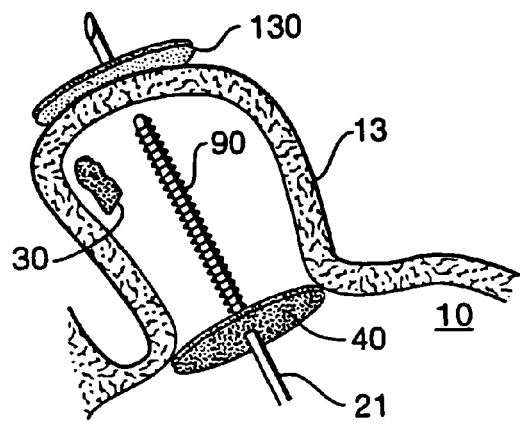
FIG. 16 is a partial cross sectional view of a portion of a heart showing an atrium and its associated atrial appendage having a disk, a membrane and a spring therebetween.

FIG. 16 shows the device of FIG. 15 applied to the left atrial appendage 13 having thrombus 30. After the device is applied the spring 90, pulls the disk 130 toward the porous membrane 40 collapsing the left atrial appendage 13 and trapping the thrombus 30 therein as shown in FIG. 17.

Figure 17:
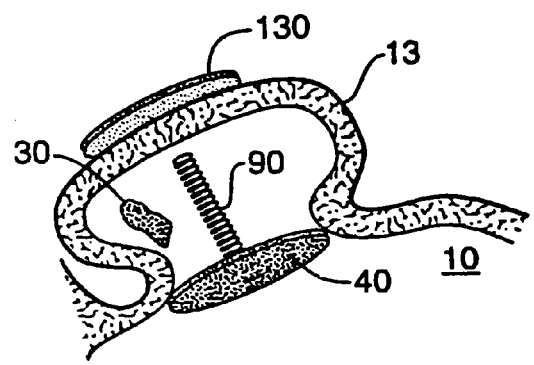
FIG. 17 is a partial cross sectional view of a portion of a heart showing an atrium and its associated atrial appendage shown in a collapsed position.
Figure 18:
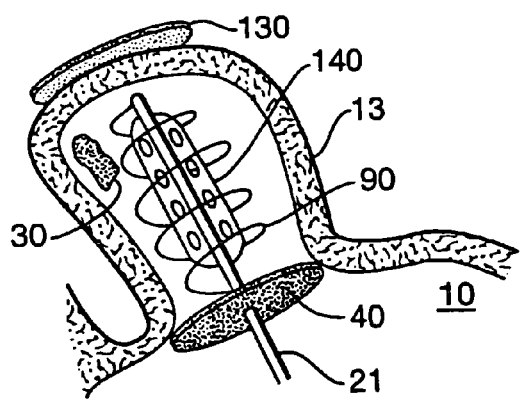
FIG. 18 is a partial cross sectional view of a portion of a heart showing an atrium and its associated atrial appendage having a disk, a spring, a membrane and vacuum in the catheter.

FIG. 18 shows an alternate embodiment of the device in FIGS. 16 and 17 wherein the catheter 21 is equipped with a vacuum 140 for sucking out blood and thrombosis 30 found in the left atrial appendage 13. The vacuum 140 will help collapse the left atrial appendage 13 such that spring 90 need not be as large as in FIG. 16.

Figure 19:
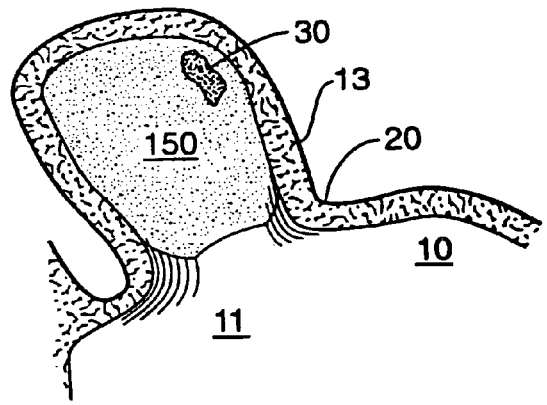
FIG. 19 is a partial cross sectional view of a portion of a heart showing an atrium and its associated atrial appendage having a membrane material filling the atrial appendage.

FIG. 19 shows an alternative embodiment of the device where the membrane 150 is inserted into the left atrial appendage 13 and fills it securing the membrane 150 therein. The membrane 150 may be delivered in a catheter as a compressed material and expanded in the atrial appendage 13 or be delivered in a liquid form which will fill the atrial appendage and be transformed into a membrane by curing with another chemical delivered by the catheter or with the aid of a UV light supplied through a fiber optic cable in the catheter 21. By filling the left atrial appendage 13 with a membrane material 150 no blood can enter to pool and become a thrombus 30 and no thrombus 30 can exit to cause heart attacks, strokes and ischemia.

Figure 20:
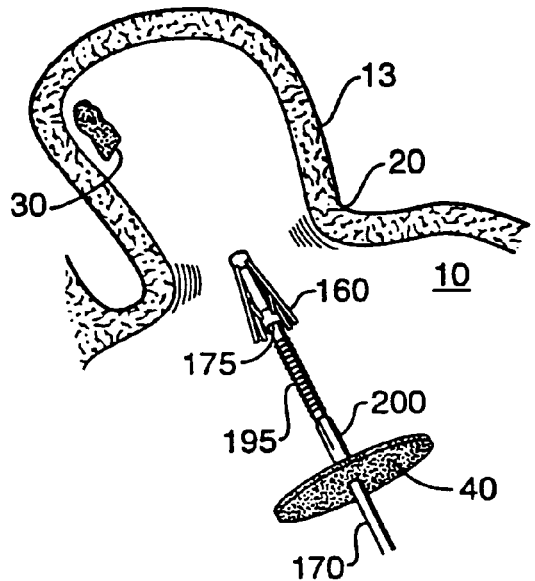
FIG. 20 is a partial cross sectional view of a portion of a heart showing an atrium and its associated atrial appendage showing an umbrella folded for entering the atrial appendage.
Figure 21:
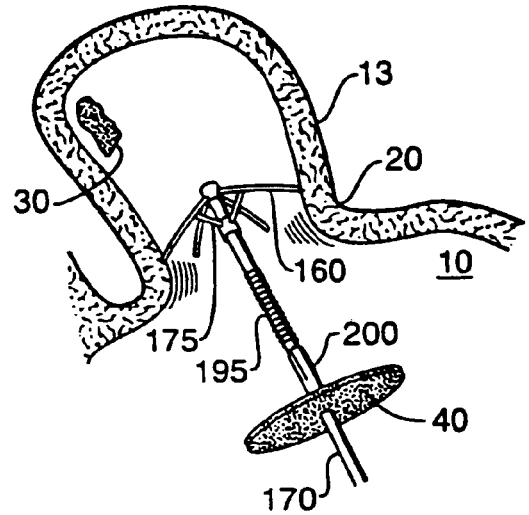
FIG. 21 is a partial cross sectional view of a portion of a heart showing an atrium and its associated atrial appendage showing the umbrella opened in the atrial appendage to secure the umbrella into the wall of the atrial appendage.
Figure 22:
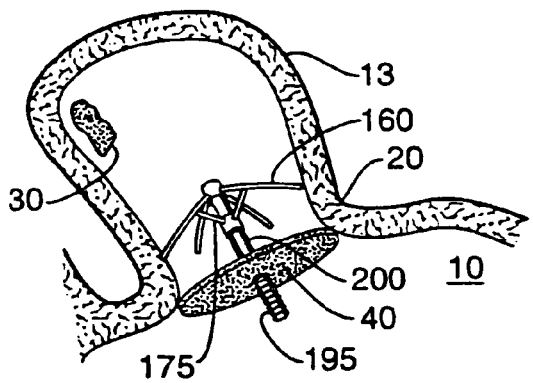
FIG. 22 is a partial cross sectional view of a portion of a heart showing an atrium and its associated atrial appendage showing the umbrella and membrane sealing the ostium of the atrial appendage.

FIGS. 20-22 show another embodiment of the invention using an umbrella principle for securing the membrane 40 against the ostium 20. FIG. 20 shows closed umbrella struts 160 entering the ostium 20 of left atrial appendage 13. The membrane 40 is some distance back from the umbrella struts 160 at the bottom of the range of teeth 195 on pole 170. FIG. 21 shows the umbrella struts inside of the left atrial appendage 13 with the struts 160 open. Umbrella opening structure 175 on pole 170 pushes the struts out to the umbrella open position. The umbrella opening structure 175 can be pushed to the open position or have a spring-loaded mechanism to push the struts 160 to the open position. The ends of the umbrella struts 160 engage the left atrial appendage wall around the ostium 20 and prevent the umbrella from being withdrawn from the left atrial appendage 13. The ends of the umbrella struts 160 that engage the atrial appendage wall may be blunted or have bulbs on the tips or have padding so as not to puncture the left atrial appendage 13. FIG. 22 shows the membrane 40 drawn up against the ostium 20 by ratcheting the membrane along pole 170. The pawl mechanism 200 engages teeth 195 on pole 170 and is moved forward to snuggly block the ostium 20 with the membrane 40.

Figure 23:
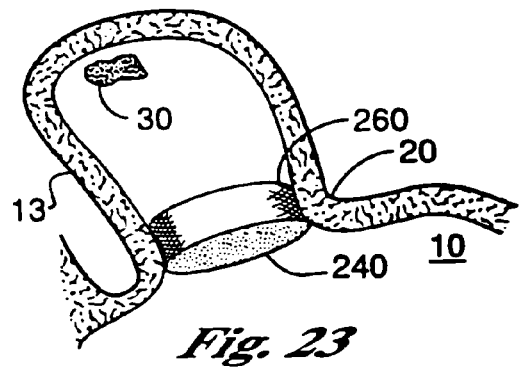
FIG. 23 is a partial cross sectional view of a portion of a heart showing an atrium and its associated atrial appendage showing a stent having a membrane for blocking the ostium of the atrial appendage.

FIG. 23 shows a stent 260 applied to the ostium 20 of left atrial appendage 13. The stent 260 expands after leaving a delivery catheter such that the wall of the stent secures the stent by pressure to the ostium 20. Membrane 240 folds or is compressed into the delivery catheter and expands as the stent 260 expands and lodges in the ostium 20 of the left atrial appendage 13.

Figure 24:
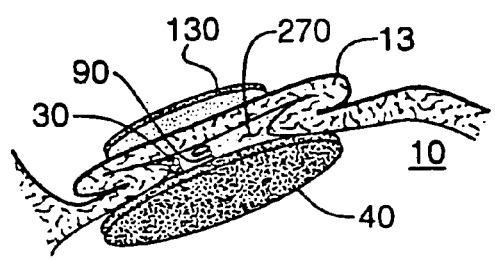
FIG. 24 is a partial cross sectional view of a portion of a heart showing an atrium and its associated atrial appendage showing the atrial appendage reduced to a minimum volume by a disk and spring squeezing the appendage against a membrane.

FIG. 24 shows the left atrial appendage 13 compressed such that the volume of the atrial appendage is reduced to almost nothing. With the volume reduced the atrial appendage will not have a large volume of blood which can produce a thrombus. In the embodiment shown disk 130 and spring 90 pull the left atrial appendage 13 toward membrane 40. Although FIG. 24 shows the use of a disk 130 and spring 90 to act on the left appendage any method to reduce the volume of the atrial appendage as much as possible may be used. In addition to physically reducing the volume a substance 270 may be injected into the appendage to further limit its volume, or to clot the blood already present therein.

As shown in FIG. 24 the membrane 40 is much larger than the ostium 20. The over-size membrane 40 may be used in all embodiments to ensure that the ostium 20 is completely blocked.

The devices described above may be percutaneously delivered to the left and tight atrial appendages 13, 23 respectively. The devices may have materials in them which enhance vision or imaging by ultrasound, x-ray or other means making it easier for the device to be implanted and accurately centered over the ostium 20 of the atrial appendage 13. This may consist of small beads placed strategically on the membrane, the connecting elements, or on the anchors. Referring to FIG. 1 catheter 21 is seen entering the heart by way of the aorta 12 to the left ventricle 16 passing through the mitral valve 17 and then entering the left atrial appendage 13 to apply the porous membrane 40 in one of the embodiments as disclosed above. In FIG. 2 the catheter 21 enters the heart from the femoral vein, passes through the inferior vena cava 18 to the right atrium and then passes through the fossa ovalis 19 or through the septum 29 into the left atrium 11 and then approaches the left atrial appendage 13 to apply the porous membrane 40 thereto. FIG. 3 shows the catheter 21 being applied to the right atrial appendage 23. Catheter 21 may enter the heart through the jugular vein 28 or the femoral vein to the inferior vena cava 18.

It should be understood that the invention may be practiced with numerous means of attaching the membrane 40 to cover the ostium 20 of the atrial appendages 13 and 23. Any combination of the attachment means with adhesives, prongs, stents, anchors, disks, tethers or springs may be used. The membrane may also be inside of the atrial appendages 13 and 23, or may penetrate the atrial appendage and provide a means to securely lock the membrane device into place. Other means of providing a membrane for blocking blood flow into and blood clots out of the atrial appendages not listed may also be used. A substance may be injected into the appendage to limit its volume, or to clot the blood already present.

In all of the above embodiments the blood of the appendage may be facilitated to clot in order to form a large, immobile mass. Alternatively, the appendage may be filled with any substance that will occupy volume. Examples are fibrin, prosthetic polymers (PLLA), Silicone, or a balloon that is delivered and remains in place for long periods of time.

All of the above embodiments shown and discussed for the left atrial appendage 13 are also useable on the right atrial appendage 23. Further the invention may be used to close fistulae or connections elsewhere in the body such as the colon or bronchopulmonary systems. The invention may also be used to seal false aneurysms. When the membrane is placed in a false aneurysm it will strengthen the defect and may help to avoid surgery.

Obviously, many modifications and variations of the present invention are possible in light of the above teachings. It is therefore to be understood that, within the scope of the appended claims, the invention may be practiced otherwise than as specifically described.

What is claimed is:

1. A method of preventing thrombus in the atrial appendage of a patient from entering the blood stream, said method comprising:
   providing a membrane between the atrial appendage and the atrium;
   securing the membrane over an ostium of the atrial appendage by extending at least two engagement members substantially radially outwardly from adjacent an edge of the membrane into the atrial appendage through the ostium of the atrial appendage;
   piercing the wall of the atrial appendage with the engagement members extending radially into the atrial appendage wall substantially adjacent the ostium to secure the membrane in place; and
   further securing the membrane over the ostium of the atrial appendage adhesively; thereby:
   blocking blood flow to prevent thrombus from flowing between the atrial appendage and the atrium.

2. A method of preventing atrial appendage thrombus from entering the blood stream comprising:
   providing a membrane between the atrial appendage and the atrium;
   securing the membrane over an ostium of the atrial appendage by extending at least two engagement members substantially radially outwardly from adjacent an edge of the membrane into the atrial appendage through the ostium of the atrial appendage;

piercing the wall of the atrial appendage with the engagement members extending radially into the atrial appendage wall substantially adjacent the ostium to secure the membrane in place; and further attaching the membrane to the ostium with an adhesive; thereby:

blocking blood flow to prevent thrombus from flowing between the atrial appendage and the atrium.

3. A method of preventing atrial appendage thrombus from entering the blood stream comprising:

providing a membrane between the atrial appendage and the atrium;

securing the membrane over an ostium of the atrial appendage by extending at least two engagement members substantially outwardly from adjacent an edge of the membrane into the atrial appendage through the ostium of the atrial appendage;

piercing the wall of the atrial appendage with the engagement members extending radially into the atrial appendage wall substantially adjacent the ostium to secure the membrane in place; and providing a means for centering the membrane over the ostium of the atrial appendage to provide a seal, by attaching a centering rim to the membrane for insertion into the ostium of the atrial appendage; thereby:

blocking blood flow to prevent thrombus from flowing between the atrial appendage and the atrium.

4. A method of preventing thrombus in the atrial appendage of a patient from entering the blood stream, said method comprising:

providing a filter membrane between the atrial appendage and the atrium;

securing the filter membrane over an ostium of the atrial appendage by extending at least two engagement members substantially outwardly from adjacent an edge of the filter membrane into the atrial appendage through the ostium of the atrial appendage;

piercing the wall of the atrial appendage with the engagement members extending radially into the atrial appendage wall substantially adjacent the ostium to secure the filter membrane in place; and further securing the filter membrane over the ostium of the atrial appendage adhesively; thereby:

filtering blood flow to prevent thrombus from flowing between the atrial appendage and the atrium.

5. A method of preventing atrial appendage thrombus from entering the blood stream comprising:

providing a filter membrane between the atrial appendage and the atrium;

securing the filter membrane over an ostium of the atrial appendage by extending at least two engagement members substantially radially outwardly from adjacent an edge of the filter membrane into the atrial appendage through the ostium of the atrial appendage;

piercing the wall of the atrial appendage with the engagement members extending radially into the atrial appendage wall substantially adjacent the ostium to secure the filter membrane in place; and further attaching the filter membrane to the ostium with an adhesive; thereby:

filtering blood flow to prevent thrombus from flowing between the atrial appendage and the atrium.

6. A method of preventing atrial appendage thrombus from entering the blood stream comprising:

providing a filter membrane between the atrial appendage and the atrium;

securing the filter membrane over an ostium of the atrial appendage by extending at least two engagement members substantially radially outwardly from adjacent an edge of the filter membrane into the atrial appendage through the ostium of the atrial appendage;

piercing the wall of the atrial appendage with the engagement members extending radially into the atrial appendage wall substantially adjacent the ostium to secure the filter membrane in place; and providing a means for centering the filter membrane over the ostium of the atrial appendage to provide a seal, by attaching a centering rim to the filter membrane for insertion into the ostium of the atrial appendage; thereby:

filtering blood flow to prevent thrombus from flowing between the atrial appendage and the atrium.

7. A method of preventing atrial appendage thrombus from entering the blood stream comprising:

providing a membrane;

securing the membrane over an ostium of the atrial appendage by extending prongs from adjacent an edge of the membrane into the atrial appendage through the ostium;

piercing the wall of the atrial appendage with the prongs extending radially into the atrial appendage wall substantially adjacent the ostium to secure the membrane in place; and further securing the membrane over the ostium of the atrial appendage adhesively; thereby:

blocking the atrial appendage ostium with the membrane preventing blood from entering the atrial appendage and forming thrombus therein and preventing thrombus formed therein from leaving.

8. A method of preventing atrial appendage thrombus from entering the blood stream comprising:

providing a membrane;

securing the membrane over an ostium of the atrial appendage by extending prongs from adjacent an edge of the membrane radially into the atrial appendage through the ostium;

piercing the wall of the atrial appendage with the prongs extending into the atrial appendage wall substantially adjacent the ostium to secure the membrane in place; and vacuuming the atrial appendage for removing thrombus from therein and for collapsing the membrane; thereby:

blocking the atrial appendage ostium with the membrane preventing blood from entering the atrial appendage and forming thrombus therein and preventing thrombus formed therein from leaving.

9. A method for preventing atrial appendage thrombus from entering the blood stream comprising:

providing a membrane;

securing the membrane over an ostium of the atrial appendage by extending prongs from adjacent an edge of the membrane into the atrial appendage through the ostium;

radially piercing the wall of the atrial appendage with the prongs extending into the atrial appendage wall substantially adjacent the ostium to secure the membrane in place; and providing a means for centering the membrane over the ostium to provide a good seal, by attaching a centering rim to the membrane for insertion into the ostium of the atrial appendage; thereby:

blocking the atrial appendage ostium with the membrane preventing blood from entering the atrial appendage and forming thrombus therein and preventing thrombus formed therein from leaving.

10. A method for preventing atrial appendage thrombus from entering the blood stream comprising:
   providing a membrane;
   securing the membrane over an ostium of the atrial appendage by extending prongs from adjacent an edge of the membrane into the atrial appendage through the ostium;
   radially piercing the wall of the atrial appendage with the prongs extending into the atrial appendage wall substantially adjacent the ostium to secure the membrane in place; and
   attaching markers to the membrane for observing the position of the membrane as it is placed in the ostium of the atrial appendage; thereby:
   blocking the atrial appendage ostium with the membrane preventing blood from entering the atrial appendage and forming thrombus therein and preventing thrombus formed therein from leaving.

11. A method for preventing atrial appendage thrombus from entering the blood stream comprising:
   providing a membrane;
   securing the membrane over an ostium of the atrial appendage by extending prongs from adjacent an edge of the membrane into the atrial appendage through the ostium;
   radially piercing the wall of the atrial appendage with the prongs extending into the atrial appendage wall substantially adjacent the ostium to secure the membrane in place; and
   attaching sensors to the membrane for providing information about the patient; thereby:
   blocking the atrial appendage ostium with the membrane preventing blood from entering the atrial appendage and forming thrombus therein and preventing thrombus formed therein from leaving.

* * * * *